(12) United States Patent
Ichihara et al.

(10) Patent No.: US 9,169,225 B2
(45) Date of Patent: Oct. 27, 2015

(54) METHOD FOR PRODUCING HEXAFLUOROPROPYLENE OXIDE

(75) Inventors: Kazuyoshi Ichihara, Osaka (JP); Hideki Nakaya, Osaka (JP); Mai Hirai, Osaka (JP); Yasuhide Senba, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 107 days.

(21) Appl. No.: 13/257,176

(22) PCT Filed: Mar. 9, 2010

(86) PCT No.: PCT/JP2010/053858
§ 371 (c)(1),
(2), (4) Date: Sep. 16, 2011

(87) PCT Pub. No.: WO2010/106942
PCT Pub. Date: Sep. 23, 2010

(65) Prior Publication Data
US 2012/0016142 A1    Jan. 19, 2012

(30) Foreign Application Priority Data
Mar. 17, 2009  (JP) .............................. P 2009-064137

(51) Int. Cl.
*C07D 303/08* (2006.01)
*C07D 301/03* (2006.01)
*C07D 303/48* (2006.01)

(52) U.S. Cl.
CPC ............ *C07D 301/03* (2013.01); *C07D 303/08* (2013.01); *C07D 303/48* (2013.01)

(58) Field of Classification Search
CPC .................................................... C07D 303/08
See application file for complete search history.

(56) References Cited

U.S. PATENT DOCUMENTS

| | | |
|---|---|---|
| 2003/0055293 A1 | 3/2003 | Wurziger et al. |
| 2010/0016615 A1 | 1/2010 | Nakaya et al. |

FOREIGN PATENT DOCUMENTS

| | | |
|---|---|---|
| EP | 0064293 | * 10/1982 |
| EP | 0 064 293 A1 | 11/1982 |
| EP | 0 473 398 A1 | 3/1992 |
| JP | 64-11021 B2 | 2/1989 |
| JP | 3-75546 B2 | 12/1991 |
| JP | 4-247078 A | 9/1992 |
| JP | 2001-521816 A | 11/2001 |
| JP | 2003-532646 A | 11/2003 |
| WO | WO 99/22857 A1 | 5/1999 |
| WO | WO 2008/050760 | * 5/2008 |
| WO | WO 2008/050760 A1 | 5/2008 |

OTHER PUBLICATIONS

Kolenko et al. (Izvestiya Akademii Nauk SSSR, Seriya Khimicheskaya, No. 11, pp. 2509-2512, Nov. 1979).*
Jahnisch et al. (Angew. Chem. Int. Ed. 2004, 43, 406-446).*
Roberge et al. (Chem. Eng. Technol. 2005, 28, No. 3; p. 318-323).*
International Preliminary Report on Patentability, issued on Oct. 18, 2011, in corresponding International Application No. PCT/JP2010/053858.
International Search Report, dated Apr. 6, 2010, issued in corresponding International Application No. PCT/JP2010/053858.
Kobayashi et al., "Micro-Reactor no Ekiso Hanno ni Okeru Seiseki Hyoka", The Society of Chemical Engineers, Dai 70 Nenkai, Kenkyu Happyo Koen Yoshishu, J214, 2005, Japan.
Kolenko et al., Izvestiya Akademii Nauk SSSR, Seriya Khimicheskaya, No. 11, pp. 2509-2512, Nov. 1979.
Search Report dated Mar. 10, 2015 for European Application No. 14196760.4.

* cited by examiner

*Primary Examiner* — Valerie Rodriguez-Garcia
(74) *Attorney, Agent, or Firm* — Birch Stewart Kolasch & Birch, LLP

(57) ABSTRACT

The present invention provides a novel method for producing hexafluoropropylene oxide, which can attain a high HFPO selectivity without using a phase transfer catalyst. Hexafluoropropylene (HFP), a water-soluble and aprotic organic solvent, and an aqueous solution of an oxidizing agent are introduced into a small space, thereby bringing into contact with each other and reacting hexafluoropropylene with the oxidizing agent to obtain hexafluoropropylene oxide (HFPO).

2 Claims, 1 Drawing Sheet

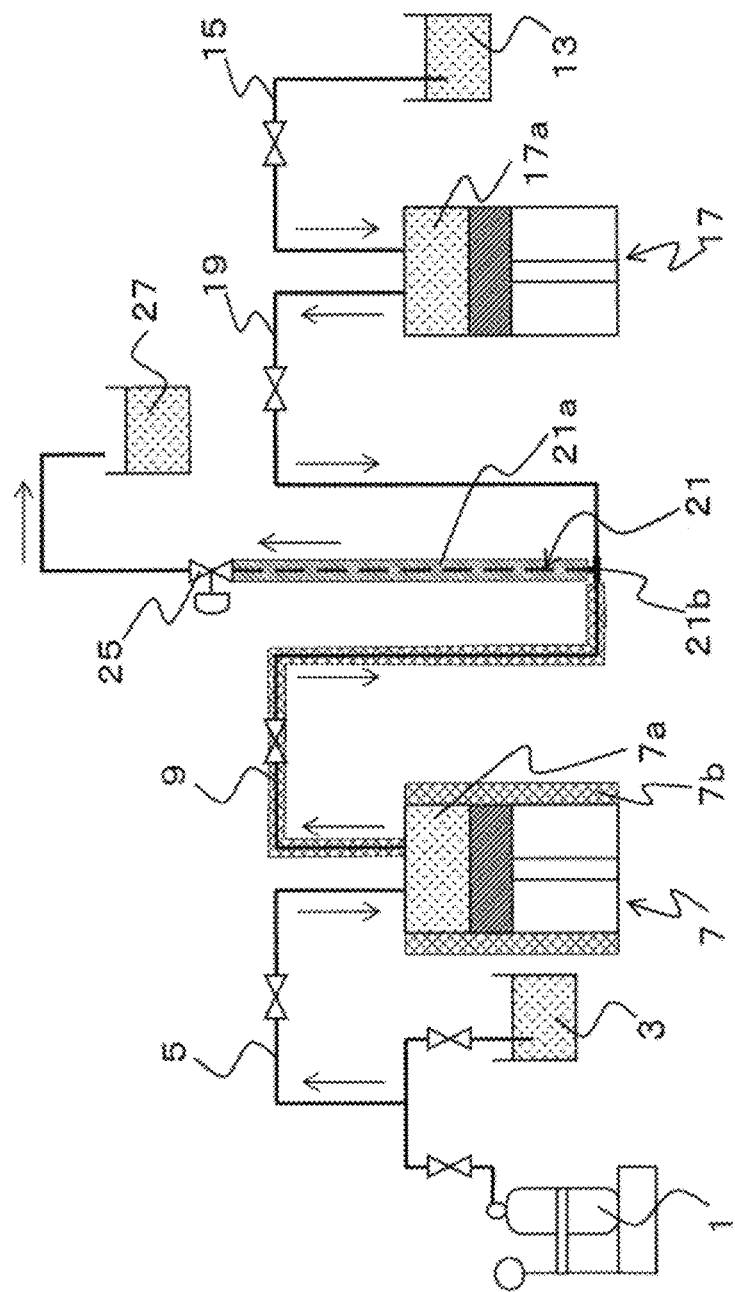

METHOD FOR PRODUCING HEXAFLUOROPROPYLENE OXIDE

TECHNICAL FIELD

The present invention relates to a method for producing hexafluoropropylene oxide, and more particularly to a method for producing hexafluoropropylene oxide by oxidation of hexafluoropropylene.

BACKGROUND ART

Hexafluoropropylene oxide is an important compound in the production of fluorine-containing compounds, since it is used, for example, as a raw material for perfluorovinyl ether. An oligomer of the hexafluoropropylene oxide is utilized as a lubricating oil, a heating medium and the like.

There has hitherto been developed, as a method for producing hexafluoropropylene oxide (hereinafter also referred to as HFPO), a method in which HFPO is obtained by oxidation of hexafluoropropyelene (hereinafter also referred to as HFP) using a hypochlorite as an oxidizing agent.

For example, there has been known method in which HFP is oxidized by a hypochlorite in a two phase system of an aqueous phase and an organic phase in the presence of a phase transfer catalyst such as a quaternary ammonium salt or a quaternary phosphonium salt to obtain HFPO (see Patent Literatures 1-3).

It has also been known that HEPO is produced from HEP when an aqueous solution of a hypochlorite is used in the presence of an aprotic solvent such as acetonitrile or diglyme.

CITATION LIST

Patent Literature

Patent Literature 1: JP 64-11021 B
Patent Literature 2: JP 3-75546 B
Patent Literature 3: WO 2008/050760

Non Patent Literature

Non Patent Literature 1: Kolenko et al., Izvestiya Akademii Nauk SSSR, Seriya Khimiche skaya, 1979, No. 11, pp 2509-2512

SUMMARY OF INVENTION

Technical Problem

In the method of obtaining HFPO by oxidizing HFP with a hypochlorite in a two phase system of an aqueous phase and an organic phase in the presence of a phase transfer catalyst such as a quaternary ammonium salt or a quaternary phosphonium salt, it is difficult to regenerate the phase transfer catalyst after use, resulting in a high cost for the phase transfer catalyst, which causes a problem of increase in the cost for the production of HFPO. In addition, practically, it requires additional steps such as the step of recovering the phase transfer catalyst after the reaction, and there is also a drawback that the process becomes complicated as a whole.

On the other hand, in the method of forming HFPO from HFP by using an aqueous solution of a hypochlorite in the presence of an aprotic solvent such as acetonitrile or diglyme, there is a problem of a low HFPO selectivity.

An object of the present invention is to provide a novel method for producing hexafluoropropylene oxide, which can attain a high HFPO selectivity without using a phase transfer catalyst.

Solution to Problem

In the known method of a type of forming HFPO from HFP using an aqueous solution of a hypochlorite in the presence of an aprotic solvent such as acetonitrile or diglyme (see Non Patent Literature 1), the reason for such a low HFPO selectivity is considered as that the formed HFPO easily reacts with water under the alkali condition to undergo decomposition (see Patent Literature 1, column 3, lines 13 to 27; and Patent Literature 2, column 3, lines 27 to 41). In contrast, the present inventors have paid an attention to the fact that the known method of this type uses a reactor of a conventional size (a reactor capable of containing about 100 mL of a reaction mixture and reacting it therein), and intensively studied, and thus the present invention has been completed.

According to one aspect of the present invention, there is provided a method for producing hexafluoropropylene oxide, which comprises introducing hexafluoropropylene (HFP), a water-soluble and aprotic organic solvent and an aqueous solution of an oxidizing agent into a small space (or a microspace), thereby bringing into contact with each other and reacting hexafluoropropylene with the oxidizing agent to obtain hexafluoropropylene oxide (HFPO).

According to the present invention, it was confirmed by experiments of the present inventors that a high HFPO selectivity is obtained without using a phase transfer catalyst (such as a quaternary ammonium salt or a quaternary phosphonium salt).

While the present invention is not intended to be bound even by any specific theory, the reason is considered to be as follows.

When a water-soluble and aprotic organic solvent and an aqueous solution of an oxidizing agent are mixed together, this organic solvent can be dissolved in water to form a dissolved phase, and can promote nucleophylic attack on a double bond of HFP by ions derived from the oxidizing agent to form HFPO.

However, when this reaction is carried out in a reactor of a conventional size, molecular contact (in other words, microscopic mixing) of ions derived from an oxidizing agent with HFP hardly occurs, so that the reaction proceeds very slowly, and a long reaction time (e.g. 100 hours) is required so as to obtain a HFP conversion rate of 40% or more. When the reaction time increases, HEPO may react with water to undergo decomposition in the meantime, and thus an amount of HFPO finally obtained is decreased. Additionally, the reaction is an exothermic reaction and, when a hot spot is formed because of insufficient removal of heat, the side reaction is likely occurs and HFP is consumed for the side reaction. As a result of these, it is considered that a high HFPO selectivity cannot be obtained.

In contrast, when such the reaction is carried out in a small space as in the present invention, molecular contact (in other words, microscopic mixing) of ions derived from the oxidizing agent with HFP can be sufficiently attained and the reaction is allowed to rapidly proceed. Therefore, the reaction time (or residence time) can be shortened, and thus the formed HFPO can be instantly discharged out of the reaction system (the small space) to prevent decomposition or further reaction (overreaction) of HFPO. Proceeding of the reaction in the small space enables effective heat removal and strict temperature control, and thus formation of a hot spot can be prevented, leading to suppression of the side reaction. As a result of these, it is considered that a high HFPO selectivity can be obtained by the present invention.

In the present invention, the "small space" (or microspace) means a space having a width of a passage of 3 cm or less, preferably not less than 1 μm and not more than 1 cm (micro-order or milli-order), through which a fluid for the reaction flows (in the present invention, the fluid includes a liquid phase mixture of hexafluoropropylene, a water-soluble and aprotic organic solvent, and an aqueous solution of an oxidizing agent, and an optionally existing vapor phase), and the width of the passage means a minimum distance between opposing wall surfaces of the passage. Such the "small space" may be each passage (or channel) of a reactor or a mixer known as a "microreactor" or a "micromixer" in the field of pharmaceutical, synthesis chemistry and the like (for example, refer to Patent Literature 3).

The "water-soluble and aprotic organic solvent" used in the present invention is any organic solvent which is at least partially dissolved in water, and is not dissociated to generate a proton (or is hardly dissociated to generate a proton).

Specifically, it is preferred to use, as the water-soluble and aprotic organic solvent, at least one selected from the group consisting of acetonitrile, glyme, and N,N-dimethylformamide. These have advantages of having a high solubility in water and being able to obtain a particularly high selectivity.

As to the aqueous solution of an oxidizing agent, there is no particular limitation thereon, but it is possible to use an aqueous solution of hypohalite or a hydrogen peroxide solution. The aqueous solution of hypohalite has an advantage of having a high ability as an oxidizing agent. The hydrogen peroxide solution has advantages of having a high ability as an oxidizing agent, being available at a lower price, and giving water as a by-product through a side reaction so that a waste thereof has less adverse impact on environment.

As the hypohalite, it is possible to use an alkali metal or an alkaline earth metal salt(s) of hypohalous acid. Specifically, it is preferred to use, as the hypohalite, at least one selected from the group consisting of sodium hypochlorite and calcium hypochlorite. Any of these hypohalites is available at a lower price.

Advantageous Effects of Invention

According to the present invention, there is provided a novel method for producing hexafluoropropylene oxide, which can attain a high HFPO selectivity without using a phase transfer catalyst.

BRIEF DESCRIPTION OF DRAWINGS

FIG. 1 is a schematic view of an apparatus used to produce HFPO in Examples of the present invention.

DESCRIPTION OF EMBODIMENTS

The method for producing hexafluoropropylene oxide (HFPO) in an embodiment of the present invention will be described in detail below.

First, hexafluoropropylene (HFP), a water-soluble and aprotic organic solvent, and an aqueous solution of an oxidizing agent are prepared.

Hexafluoropropylene (HFP) as a reaction raw material may be obtained, for example, from tetrafluoroethylene or the like, but not limited thereto.

The water-soluble and aprotic organic solvent is composed of an organic compound(s) which is at least partially dissolved in water. Preferred water-soluble and aprotic organic solvent is such that all of the organic solvent to be used is able to be dissolved in water to form a uniform phase, but not limited thereto. Also, the water-soluble and aprotic organic solvent is composed of an organic compound(s) which is not dissociated to generate a proton (or is hardly dissociated to generate a proton), and typically does not have a hydrogen atom bound to an atom having large electronegativity (nitrogen and oxygen atoms, etc.).

Examples of such the organic solvent include nitrile (acetonitrile, propionitrile etc.), glyme (monoglyme (1,2-dimethoxyethane), diglyme, triglyme, tetraglyme), N,N-dimethylformamide (DMF), N,N-dimethylacetamide (DMA), dimethyl sulfoxide (DMSO), hexamethylphosphoric acid triamide (HMPA), dioxane, acetone, sulfolane and the like.

Among them, it is preferable to use acetonitrile, glyme and N,N-dimethylformamide alone or at least two of them in combination.

The ratio of HFP and the organic solvent can be appropriately selected. For example, the amount of HFP is from about 1 to 500 g, and preferably from about 10 to 300 g per 1 L of the organic solvent.

In the present embodiment, HFP and the organic solvent are mixed together in advance to prepare an organic phase. It is noted, however, that this is not essential to the present invention.

Solubility of HFP in the organic solvent may depend on the temperature and pressure conditions, depending on the kind of the organic solvent used. It is preferred that prior to supply of the organic phase containing HFP to a small space, this organic phase (or in the state where HFP and the organic solvent are allowed to coexist) is subjected to substantially the same or closer conditions to temperature and pressure conditions in the small space (this is also referred to as preliminary adjustment in the present description). For example, the organic phase may be preliminary maintained at a temperature of about −40 to 100° C., preferably −20 to 50° C., under a pressure of about 0.0 to 10 MPaG (gauze pressure), preferably about 0.0 to 2 MPaG (gauze pressure), appropriately. This preliminary adjustment conditions are preferably temperature and pressure condition under which HFP is substantially in a liquid state. In order to proceed a liquid phase reaction effectively, it is more preferable to dissolve HFP as a reaction raw material in the organic phase as much as possible. However, since HFP is a gas at a normal temperature under a normal pressure (boiling point of −29.4° C.), it is preferable that on supplying the organic phase into the small space, the organic phase is preliminary subjected to temperature and pressure conditions under which HFP is substantially in a liquid state, thereby dissolving more HFP, desirably substantially the entire HFP in the organic phase. The temperature and pressure conditions for the preliminary adjustment may be different from those of the small space into which the organic phase to be supplied, since a reaction time (residence time) in the small space is very short so that redistribution of HFP from the organic phase to a vapor phase during the reaction time is negligible as described below.

As the aqueous phase, on the other hand, an aqueous solution of an oxidizing agent is prepared. For the aqueous solution of an oxidizing agent, an aqueous solution of hypohalite or a hydrogen peroxide solution can be used. The hypohalite can be, for example, an alkali metal salt or an alkaline earth metal salt of hypohalous acid represented by $M(OX)_n$ (wherein M is an alkali metal or an alkaline earth metal, preferably Na or Ca, X is halogen, preferably Cl, and n is 1 or 2 depending on valence of M).

Among hypohalites, a hypochlorite is preferred since it generates a hypochlorous acid ion under the reaction condition and it is converted into a chlorine ion by reacting with HFP to form a salt having no oxidation activity. A sodium salt and a calcium salt of hypochlorous acid are preferable since they are industrially mass-produced for use in a bleaching agent, a sanitizing agent and the like, and are available at a lower price. Among them, the sodium salt is particularly preferred since it has high water-solubility and is less likely to cause clogging of a piping or the like. The hydrogen peroxide solution is preferred since it has less adverse impact on environment.

In order to stably generate a hypohalous acid ion or a hydrogen peroxide ion and to prevent the oxidizing agent from being decomposed with an acid generated by the reaction, an alkali can be added to the aqueous solution of the oxidizing agent. As such the alkali, there is, for example, $M(OH)_n$ (wherein M is an alkali metal or an alkaline earth metal, preferably Na or Ca, and n is 1 or 2 depending on valence of M).

The concentration of the oxidizing agent in the aqueous solution can be appropriately selected. Upon supply to the small space (or at an initial stage of the reaction), in the case of the hypohalite as an example, an effective halogen concentration is from about 1 to 20% by weight, and preferably from about 5 to 15% by weight; and in the case of hydrogen peroxide as another example, the hydrogen peroxide concentration is from about 1 to 80% by weight, and preferably from about 5 to 60% by weight.

Then, the organic phase and the aqueous phase thus prepared are supplied to the small space. For example, HFP and the organic solvent may be continuously mixed together, and the thus obtained mixture (organic phase) and a separately prepared aqueous solution of the oxidizing agent (aqueous phase) may be continuously supplied to the small space and mixed together to perform a reaction.

The small space may have a width of a passage, through which a fluid for the reaction flows (the fluid is comprised of the liquid phase and a vapor phase which may optionally exist), of 3 cm or less. For example, the width of the passage can be from about 1 µm to 1 cm, and preferably from about 10 to 5,000 µm. As long as the width of the passage is within the above range, there is no particular limitation on the length and cross-sectional area of the passage. The cross-sectional area of the passage can be, for example, from about $3.1 \times 10^{-6}$ to $7.9 \times 10^{-1}$ cm². For example, a reactor (or reaction tube) having at least one small space with an equivalent diameter of 20 µm to 2,000 µm, or a so-called "microreactor" or "micromixer" can be used.

The passage defining the small space may be formed of, for example, metal, preferably corrosion-resistant metal such as SUS (SUS316, SUS316L, SUS304 etc.), Hastelloy, Monel and Inconel. In another example, the passage defining the small space may be formed of glass or a fluorine resin (tetrafluoroethylene/hexafluoropropylene copolymer (FEP), tetrafluoroethylene/perfluoroalkyl vinyl ether copolymer (PFA), polytetrafluoroethylene (PTFE), polyvinylidene fluoride (PVdF), polychlorotrifluoroethylene (PCTFE), polyvinyl fluoride (PVF), etc.). The glass and fluorine resin exhibit further higher corrosion resistance than the above corrosion-resistance metal, and can substantially prevent the oxidizing agent from being consumed by corrosion. In addition, when transparent glass is used, appearance therein can be observed from the outside.

By supplying the organic phase and the aqueous phase to the small space as described above, HFP, the water-soluble and aprotic organic solvent, and the aqueous solution of the oxidizing agent pass through the small space and are contacted with each other, during which HFP reacts with the oxidizing agent to generate HFPO.

More specifically, while HFP, the water-soluble and aprotic organic solvent, and the aqueous solution of the oxidizing agent pass through the small space, the organic solvent is dissolved in the aqueous solution to form a mixed liquid phase. The mixed liquid phase is preferably forming a uniform phase, but the mixed liquid phase may be separated into two phases by the salting-out effect (which is cased typically in the case of using a hypohalite as the oxidizing agent) or the like. At this step, HFP is considered to be present while being dissolved in the water-soluble and aprotic organic solvent, but not limited thereto. HFP and the oxidizing agent are able to be molecularly contacted in this mixed liquid phase, preferably, in the uniform phase, whereby, the following reaction (the case of hypohalite is shown exemplarily) can proceed to generate HFPO. The oxidizing agent is considered to be in the state of an ion in this reaction, but it is not limited to this and may be in the arbitrary state.

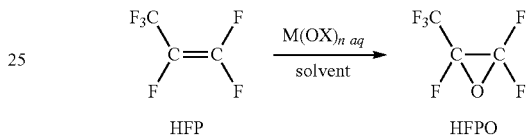

The ratio of supply flow rates of the organic phase/the aqueous phase can be appropriately set depending on a specific situation and is, for examples, from about 0.1 to 10, and preferably from about 0.2 to 5.

The temperature and pressure in the small space are not particularly limited as long as the reaction for obtaining HFPO from HFP proceeds, and can be appropriately maintained at a temperature of about −40 to 100° C., preferably about −20 to 50° C. and a pressure of about 0.0 to 10 MPaG (gauze pressure), preferably about 0.0 to 2 MPaG (gauze pressure). The temperature and/or pressure exceeding 100° C. and/or 10 MPaG (gauze pressure) is not preferable from the viewpoint of the matters of pressure resistance and corrosion resistance, safety, and the apparatus cost. In contrast, the temperature and/or pressure lower than −40° C. and/or 0.0 MPaG (gauze pressure) is not preferable since this tends to precipitate solid readily and may cause clogging of a piping or the like.

The reaction time (or residence time) in the small space is able to be extremely shorter time as compared with a conventional method, and can be, for example, about 0.01 to 1,000 seconds, particularly about 0.01 to 100 second, further about 0.01 to 50 seconds.

The liquid phase (reaction mixture) after the reaction is taken out of the small space. Since HFPO is gasified by depressurization, HFPO can be easily recovered from the resulting liquid phase (reaction mixture). Additionally, the liquid phase after the reaction may be optionally subjected to a post-treatment to separate unreacted HFP, by-product(s) from a side reaction and the organic solvent. When an aqueous solution of a hypohalite $M(OX)_n$ is used as the aqueous solution of the oxidizing agent, examples of the by-product(s) from a side reaction include $CO_2$, $M(OH)$, $MX_n$, $MF_n$, and $(CF_3COO)_nM$ (wherein M is an alkali metal or an alkaline earth metal, preferably Na or Ca, and n is 1 or 2 depending on valence of M). Particularly when calcium hypohalite is used, $CaF_2$ precipitates. When a hydrogen peroxide solution is used as the aqueous solution of the oxidizing agent, examples of the by-product(s) from a side reaction include $CO_2$, $H_2O$, $MF_n$, and $(CF_3COO)_nM$ (wherein M is an alkali metal or an alkaline earth metal, preferably Na or Ca, and can be derived from an alkali when it is added as described above, the same shall apply in the present description).

In order to purify the reaction mixture, known methods such as distillation, extraction, column chromatography, membrane separation and recrystallization may be used. Among these methods, distillation is used industrially and widely as a general separation operation. However, the unreacted HFP and HFPO as the objective product, which are main components of the reaction mixture, have boiling points of −29.4° C. and −27.4° C. (both under the atmospheric pressure), respectively. Due to closeness of the boiling points, it is difficult to separate them from each other by a distillation operation. Therefore, in order to separate HFP from HFPO to obtain high-purity HFPO, it is preferable to perform extraction distillation. HFP separated thereby may be reused as a reaction raw material.

Thus, hexafluoropropyelne oxide is produced by the above procedure. This method for producing hexafluoropropylene oxide can be performed in a continuous manner.

The organic phase including HFP and the organic solvent may contain other component, in addition to HFP and the organic solvent. For example, when the reaction mixture is reused, optionally after the treatment such as purification, the organic phase may contain water, the oxidizing agent and the above by-product(s) from a side reaction, more specifically $M(OH)_n$, $MX_n$, $MF_n$ and $(CF_3COO)_nM$ (wherein M is an alkali metal or an alkali earth metal, preferably Na or Ca, X is halogen, preferably Cl, and n is 1 or 2 depending on valence of M) when an aqueous solution of hypohalite $M(OX)_n$ is used as the aqueous solution of the oxidizing agent. However, the additional component is not limited thereto and the organic phase may contain another component, for example, an additive such as a surfactant.

Also, the aqueous solution of the oxidizing agent (aqueous phase) may contain other component, in addition to the oxidizing agent and water, as well as the alkali which is optionally added. For example, when the reaction mixture is reused, optionally after the treatment such as purification, the aqueous phase may contain HFP, the organic solvent and the above by-product(s) from a side reaction, more specifically $M(OH)_n$, $MX_n$, $MF_n$, and $(CF_3COO)_nM$ (wherein M is an alkali metal or an alkaline earth metal, preferably Na or Ca, X is halogen, preferably Cl, and n is 1 or 2 depending on valence of M) when an aqueous solution of hypohalite $M(OX)_n$ is used as the aqueous solution of the oxidizing agent.

According to the present embodiment, a high HFPO selectivity, for example, a HFPO selectivity of 80% or more, preferably 90% or more can be obtained. Furthermore, according to the present embodiment, depending on the water-soluble and aprotic organic solvent and the aqueous solution of the oxidizing agent to be used, a high HFP conversion rate in addition to a high HFPO selectivity can be obtained and thus it becomes possible to obtain a high HFPO yield.

In the method of the present embodiment, since a phase transfer catalyst is not used, HFPO can be produced by a simple process and at lower cost.

While one embodiment of the present invention was described above, the present invention is not limited to the above embodiment and various modifications can be made.

For example, on supplying HFP, the water-soluble and aprotic organic solvent and the aqueous solution of the oxidizing agent to the small space in the above embodiment, HFP is preliminary added to the water-soluble and aprotic organic solvent to form the organic phase while the aqueous solution of the oxidizing agent is used as the aqueous phase, and these organic phase and aqueous phase are supplied separately. However, the manner of supply is not limited thereto, and it is preferable that HFP and the aqueous solution of the oxidizing agent are firstly contacted with each other on being supplied into the small space. For example, HFP, the water-soluble and aprotic organic solvent and the aqueous solution of the oxidizing agent may be supplied separately. Alternatively, while HFP is used as the organic phase, the water-soluble and aprotic organic solvent and the aqueous solution of the oxidizing agent are preliminary mixed together to form a mixed liquid phase (preferably a uniform phase, but which may be in a finely dispersed state when the mixture becomes non-uniform because of the solubility), and these organic phase and mixed liquid phase may be supplied separately.

EXAMPLES

Examples of the present invention will be described in detail below with reference to the accompanying drawings.

Example 1

Referring to FIG. 1, this Example relates to utilization of an internal space of a narrow tube 21 (shown by a dotted line in the drawing) as the small space. As the narrow tube 21, a tube made of SUS316 of 1.0 mm in a nominal internal diameter and 0.5 m in a length was used. The narrow tube 21 was capable of controlling a temperature using a jacket 21A. An inlet end of this narrow tube 21 was connected to a T-type connector 21b made of SUS (adaptable external diameter of 1/16 inch, manufactured by Swagelok Company), thus making it possible to combine and supply two kinds of fluids of an organic phase and an aqueous phase to the narrow tube 21 from lines 9 and 19, respectively. At the connections, appropriate members such as nuts were used.

Firstly, as shown in FIG. 1, HFP was drawn from an HFP bomb 1, and an organic solvent (water-soluble and aprotic organic solvent) was drawn from an organic solvent vessel 3, and they were introduced into a pump chamber 7a of a syringe pump 7 through a line 5. As the organic solvent, acetonitrile was used. In the pump chamber 7a, a mixture of HFP and the organic solvent was cooled to about −5° C. with a cooling jacket 7B covering its periphery. This mixture was pushed out of the syringe chamber 7a and supplied as the organic phase to the narrow tube 21 through the line 9. A periphery of the line 9 was also cooled to about −5° C. (a cooling part of a periphery of the line 9 is shown with cross-hatching in the drawing).

The organic phase was in a state at about 5° C. under about 0.5 MPaG (gauze pressure) when it was supplied to the narrow tube 21. At this time, substantially all of HFP was liquefied and the concentration was about 67 g per 1 L of the organic solvent.

On the other hand, an aqueous solution of an oxidizing agent was drawn from an aqueous solution vessel 13 through a line 15 and introduced into a pump chamber 17a of syringe pump 17. This aqueous solution of the oxidizing agent was prepared by dissolving about 10% by weight of sodium hypochlorite (NaClO) as an oxidizing agent and 1.7% by weight of sodium hydroxide in water. This aqueous solution was pushed out of the pump chamber 17a, and supplied as the aqueous phase to the narrow tube 21 through the line 19.

The aqueous phase was in a state at about 5° C. under about 0.5 MPaG (gauze pressure) when it was supplied to the narrow tube 21. The NaClO concentration in the aqueous phase was the same concentration in the aqueous solution used.

The supply flow rate of the organic phase was about 30 mL/min, and the supply flow rate of the aqueous phase was about 30 mL/min.

The organic phase and the aqueous phase supplied to the narrow tube 21 were mixed, and flow through the small space in the narrow tube 21. At the time, the narrow tube 21 was maintained at about 10° C. by a jacket 21a, and a pressure was adjusted by a back pressure valve 25 present in the line 21. Thereby, the interior of the narrow tube 21 was maintained at about 10° C. under about 0.5 MPaG (gauze pressure).

In the small space of the narrow tube 21, HFP was reacted with NaClO to generate HFPO. It was confirmed that, as main by-products from a side reaction during the above reaction, carbon dioxide ($CO_2$) was present in a vapor phase, and sodium trifluoroacetate ($CF_3COONa$), sodium 2,3,3,3-tetrafluoropropionate ($CF_3CFHCOONa$), and sodium 2-chloro-2,3,3,3-tetrafluoropropionate ($CF_3CFClCOONa$) were present in an aqueous phase.

Referring to FIG. 1, the reaction mixture was drawn from the narrow tube 21 into a recovery vessel 27. The residence time of the fluid (including the liquid phase and an optionally existing vapor phase) in the narrow tube 21 was about 2.9 seconds.

The recovered reaction mixture was left under an atmospheric pressure at room temperature (about 21° C.) to separate into a vapor phase and a liquid phase. The vapor phase of the recovered reaction mixture was analyzed by gas chromatography, and the liquid phase was analyzed by NMR and ion chromatography, they showed that a conversion rate of HFP was 70% and a selectivity of HFPO was about 99%. As a result, a yield was about 69%. The results are shown in Table 1.

Examples 2 and 3

The same procedures as in Example 1 were carried out, except that diglyme and N,N-dimethylformamide (DMF) were respectively used as the organic solvent in place of acetonitrile. Both diglyme and N,N-dimethylformamide (DMF) are water-soluble and aprotic organic solvents. The results are also shown in Table 1.

Example 4

The same procedures as in Example 1 were carried out, except that calcium hypochlorite ($Ca(ClO)_2$) was used as the oxidizing agent in place of sodium hypochlorite (NaClO). The results are also shown in Table 1. In this Example, $CaF_2$ precipitated in the recovered reaction mixture.

Comparative Example 1

The same procedures as in Example 1 were carried out, except that 1,1-dichloro-1-fluoroethane (HCFC-141b) was used as the organic solvent in place of acetonitrile. HCFC-141b is a nonpolar organic solvent which is not dissolved in water. The results are also shown in Table 1. In this Comparative Example 1, a conversion rate was 0% (since it was lower than a detection limit of gas chromatography), proceeding of a reaction was not recognized and, therefore, a yield was 0%.

Comparative Example 2

The reaction of producing HFPO was carried out in a reactor having a conventional size.

Using an autoclave reactor made of SUS316 having a volume of 200 mL as a reactor, 3.3 g of acetonitrile as the organic solvent, 77.0 g of an aqueous solution containing 13% by weight of sodium hypochlorite (NaClO) as the aqueous solution of the oxidizing agent, and 7.0 g of an aqueous solution of 48% by weight of hydroxide (NaOH) were charged therein. After the interior of the reactor was adjusted to −0.1 MPaG (gauze pressure) and 4° C., 13 g of HFP was charged therein over 15 minutes. After charging HFP, the temperature and pressure in the reactor were maintained at 21 to 27° C. under 0.0 to 0.6 MPaG (gauze pressure), and the reaction was performed while the liquid phase was stirred. At the time when 100 hours passed after initiation of the reaction, the reaction mixture was taken out of the reactor.

The recovered reaction mixture was analyzed as in Example 1. The results are also shown in Table 1.

TABLE 1

| No. | Organic solvent | Oxidizing agent (Aqueous solution) | Selectivity (%) | Conversion rate (%) | Yield (%) |
|---|---|---|---|---|---|
| Example 1 | Acetonitrile | NaOCl | 99 | 70 | 69 |
| Example 2 | Diglyme | NaOCl | 80 | 74 | 59 |
| Example 3 | DMF | NaOCl | 86 | 43 | 37 |
| Example 4 | Acetonitrile | $Ca(OCl)_2$ | 83 | 18 | 15 |
| Comparative Example 1 | HCFC-141b | NaOCl | — | 0 | 0 |
| Comparative Example 2 | Acetonitrile | NaOCl | 8 | 40 | 32 |

Referring to Table 1, an HFPO selectivity of 80% or more was obtained in Examples 1 to 4. Particularly, an HFPO selectivity of 90% or more was obtained in Example 1. Particularly, in Examples 1 and 2 (the case where acetonitrile or diglyme was used as the water-soluble and aprotic organic solvent, and sodium hypochlorite was used as the oxidizing agent), a high HFP conversion rate and a high HFPO yield were obtained.

Industrial Applicability

Hexafluoropropylene oxide produced by the method of the present invention can be used in the production of fluorine-containing compounds such as perfluorovinyl ether, and also can be used as a lubricating oil or a heating medium in the form of an oligomer.

REFERENCE SIGNS LIST

1 HFP bomb
3 Organic solvent vessel (water-soluble and aprotic organic solvent)
5, 9, 15, 19 Line
7, 17 Syringe pump
7a, 17a Pump chamber
7b Cooling jacket
13 Aqueous solution vessel (aqueous solution of an oxidizing agent)
21 Narrow tube
21a Jacket
21b Connecter
25 Back pressure valve
27 Recovery vessel The invention clamied is:
1. A method for producing hexafluoropropylene oxide, which comprises introducing into a small space components including hexafluoropropylene, a water-soluble and aprotic organic solvent selected from the group consisting of acetonitrile, glyme and N,N-dimethylformamide, and an aqueous solution of sodium hypochlorite, thereby bringing these components into contact with each other in a dissolved phase; and reacting hexafluoropropylene with the sodium hypochlorite to obtain hexafluoropropylene oxide, wherein the method is conducted in the absence of any phase transfer catalyst.

2. The method according to claim 1, wherein the small space has a passage width of not less than 1 µm and not more than 1 cm.

* * * * *